(12) United States Patent
Carlson (10) Patent No.: US 12,161,876 B2
(45) Date of Patent: Dec. 10, 2024

(54) AMPLITUDE MODULATION FOR TUMOR TREATING FIELDS

(71) Applicant: Novocure GmbH, Root (CH)

(72) Inventor: Kristen W. Carlson, Concord, MA (US)

(73) Assignee: Novocure GmbH, Root (CH)

( * ) Notice: Subject to any disclaimer, the term of this patent is extended or adjusted under 35 U.S.C. 154(b) by 64 days.

(21) Appl. No.: 17/564,858

(22) Filed: Dec. 29, 2021

(65) Prior Publication Data

US 2022/0203111 A1    Jun. 30, 2022

Related U.S. Application Data (60) Provisional application No. 63/132,307, filed on Dec. 30, 2020.

(51) Int. Cl.
*A61N 1/40* (2006.01)

(52) U.S. Cl.
CPC ..................... *A61N 1/40* (2013.01)

(58) Field of Classification Search
CPC ....... A61N 1/40; A61N 1/36002; A61N 1/323
See application file for complete search history.

(56) References Cited

U.S. PATENT DOCUMENTS

| | | | |
|---|---|---|---|
| 7,565,205 B2 | 7/2009 | Palti | |
| 2017/0216594 A1* | 8/2017 | Grossman | .......... A61N 1/36185 |
| 2017/0281934 A1* | 10/2017 | Giladi | ...................... A61N 1/32 |
| 2019/0133683 A1 | 5/2019 | Matloubian et al. | |
| 2020/0330757 A1* | 10/2020 | Schmidt | ................... A61N 1/05 |

FOREIGN PATENT DOCUMENTS

| | | |
|---|---|---|
| CN | 110038219 A | 7/2019 |
| WO | 2019/155407 A2 | 8/2019 |

OTHER PUBLICATIONS

Wenger C., "Modeling Tumor Treating Fields (TTFields) application in single cells during metaphase and telophase," Annual International Conference of the IEEE Engineering in Medicine and Biology Society, (2015), pp. 6892-6895.
Gabriel, S., "The dielectric properties of biological tissues: III. Parametric models for the dielectric spectrum of tissues." Physics in Medicine & Biology, 1996; 41(11), pp. 2271-2293.
Kirson, E.D., "Alternating electric fields arrest cell proliferation in animal tumor models and human brain tumors," Proceedings of the National Academy of Sciences of the United States of America, 2007 (Jun. 12, 2007), 104(24), pp. 10152-10157.

* cited by examiner

*Primary Examiner* — Lynsey C Eiseman
*Assistant Examiner* — Daniel Tehrani
(74) *Attorney, Agent, or Firm* — McCarter & English, LLP; Michael A. Sartori (57) ABSTRACT

A method of applying tumor treating fields to a subject's body includes: inducing a modulated electric field between a first transducer and a second transducer to treat a tumor of the subject's body, wherein the first transducer is located at a first location of the subject's body, and wherein the second transducer is located at a second location of the subject's body.

20 Claims, 5 Drawing Sheets

AMPLITUDE MODULATION FOR TUMOR TREATING FIELDS

CROSS-REFERENCE TO RELATED APPLICATIONS

This application claims priority to the U.S. Provisional Application Ser. No. 63/132,307, filed Dec. 30, 2020, which is hereby incorporated by reference in its entirety.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into a region of interest by transducers placed directly on the patient's body and applying AC voltages between the transducers. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

Due to the effects of electrical permittivity and conductivity of the intervening tissues (e.g., hair, scalp, skull, cerebrospinal fluid surrounding the brain and within its ventricles, blood-brain-barrier, and the gray and white matter), the efficacy of TTFields can decrease. Further, layers of tissues that have different electrical conductivity and permittivity can produce unexpected capacitive effects that interfere with transmitting efficacious field strength to the target region.

SUMMARY OF THE INVENTION

One aspect of the invention is directed to a method of applying tumor treating fields to a subject's body. The method comprises inducing a modulated electric field between a first transducer and a second transducer to treat a tumor of the subject's body, wherein the first transducer is located at a first location of the subject's body, and wherein the second transducer is located at a second location of the subject's body.

DESCRIPTION OF EMBODIMENTS

The disclosed subject matter provides techniques for applying TTFields with modulated electric fields to a subject's body to improve the efficacy of TTFields. By applying modulated electric fields, the obstructive effects of frequency-dependent electrical tissue properties may be attenuated, and thus increasing electric field strength may be delivered to target tumor sites, thereby positively influencing the therapeutic effect of the TTFields.

Figure 1:
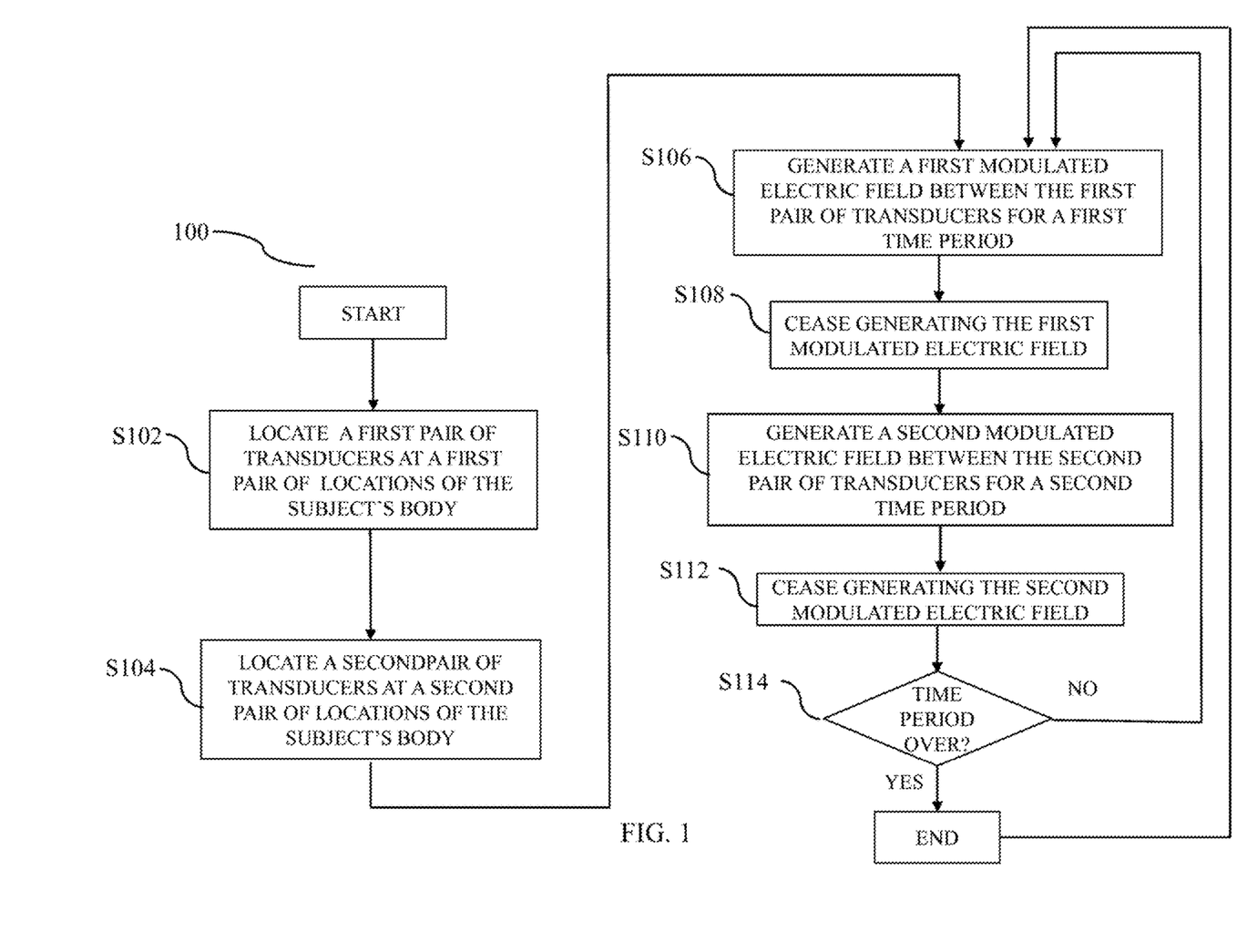
FIG. 1 is a flowchart depicting an example of applying TTFields with modulated electric fields to a subject's body.

FIG. 1 describes an example method 100 of applying TTFields with modulated electric fields to a subject's body. In one example, two modulated electric fields are alternately applied between two pairs of transducers.

With reference to FIG. 1, at step S102, method 100 comprises locating a first pair of transducers at a first pair of locations of the subject's body. In one example, the first pair of transducers comprises a first transducer and a second transducer. In one example, the first transducer is a transducer array having a first array of substantially flat electrode elements, and the second transducer is a transducer array having a first array of substantially flat electrode elements. In another example, the first and the second transducers are capacitively coupled. In another example, the first and the second transducers are not capacitively coupled. The first pair of transducers defines a first channel for the TTFields that intersects a tumor of the subject's body.

At step S104, a second pair of transducers are located at a second pair of locations of the subject's body. In one example, the second pair of transducers comprise a third transducer and a fourth transducer. The third transducer and the fourth transducer are similar to the first and second transducers discussed above. The second pair of transducers defines a second channel for the TTFields that intersects the tumor of the subject's body.

At step S106, a first modulated electric field is generated between the first pair of transducers for a first time period. The first modulated electric field is generated by a voltage generator. The first modulated electric field is produced by a first amplitude modulated AC voltage generated by the voltage generator and applied to the first pair of transducers. The amplitude modulated AC voltage may be considered to have a first modulating AC voltage and a second carrier AC voltage. The first modulating AC voltage may also be referred to as a first message AC voltage. The amplitude modulated AC voltage may be generated by having the first modulating AC voltage modulate the amplitude of the second carrier AC voltage, or may be generated as an AC voltage represented by the first modulating AC voltage modulating the amplitude of the second carrier AC voltage. The first modulated electric field is produced using the first transducer, the second transducer, and the first amplitude modulated AC voltage.

In one example, the first modulating AC voltage is capable of producing TTFields with a certain intensity (e.g., 1-20 V/cm) and a first lower frequency range (e.g., 50-500 kHz), and the second carrier AC voltage is capable of producing TTFields with a certain intensity (e.g., 1-20 V/cm) and a second higher frequency within a range that modulates frequency-dependent electrical tissue properties, (e.g., 500 kHz-10 GHz). In one example, the frequency of the first modulating AC voltage is approximately 200 kHz, and the frequency of the second carrier AC voltage is approximately 1 MHz. In one example, the electric field strength of the modulated electric field in the tumor of the subject's body is between approximately 1 V/cm and approximately 20 V/cm. In another example, the electric field strength of the modulated electric field in the tumor of the subject's body is between approximately 1 V/cm and approximately 4 V/cm. The lower field strength range may be used with a given method of controlling the temperature of tissue at the transducer site, while the higher field strength range may be used with a more effective method of controlling tissue temperature at the transducer site. In one example, the transducer may include one or more sensors (e.g., thermistors) to detect the temperature of the tissue in contact with the transducer. The first modulated electric field is generated using the first pair of transducers for the first time period (e.g., one second). The transducers may be conductive or non-conductive.

In one example, the first frequency is a frequency to disrupt mitosis in the tumor of the subject's body, and the second frequency is a frequency to attenuate obstructive effects of frequency-dependent electric tissue properties. In one example, the first frequency is selected to treat the tumor of the subject's body, and the second frequency is selected to produce a modulated electric field strength larger inside cell walls of the tumor of the subject's body than outside the cell walls of the tumor of the subject's body.

In one example, the modulated electric field includes: a first signal having a first frequency to disrupt mitosis in the tumor of the subject's body; and a second signal being a carrier signal modulated by the first signal, where the second signal has a frequency to penetrate cell walls of the tumor of the subject's body. In one example, the first frequency is selected for treating a tumor in the subject's body, and the first frequency is less than the second frequency. In one example, the modulated electric field has two simultaneous frequencies.

In one example, the first modulating AC voltage includes a message signal at a first frequency and a carrier signal at a second frequency, where the first frequency is a frequency to treat a tumor in the subject's body, and where the message signal modulates the carrier signal.

Figure 2A:
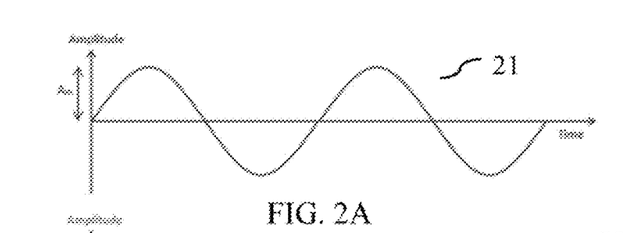
FIGS. 2A-2C depict an example of amplitude-modulated AC voltage.

FIG. 2A depicts an example of the first modulating AC voltage. In one example, the first modulating AC voltage 21 is for treating a tumor. The first modulating AC voltage may be referred to as a modulating signal or a message signal. The first modulating AC voltage 21 has a first amplitude $A_m$ and a first frequency $f_m$. In one example, the first frequency is a frequency to disrupt mitosis in the tumor of the subject's body and is within the intermediate frequency range (e.g., 50-500 kHz or 50 kHz-1 MHz). In one example, the first frequency is between approximately 100 kHz and approximately 500 kHz. In another example, the first frequency is between approximately 100 kHz and approximately 300 kHz. In another example, the first frequency is between approximately 125 kHz and approximately 250 kHz. In one example, the first frequency is approximately 200 kHz.

Figure 2B:
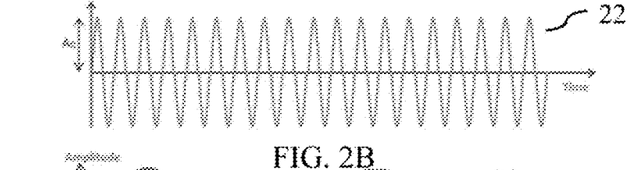

FIG. 2B depicts an example of the second carrier AC voltage. In one example, the second carrier AC voltage 22 is for penetrating the membranes of the cells of the tumor. The second carrier AC voltage may also be referred to as a carrier signal. The second carrier AC voltage 22 has a second amplitude $A_c$ and a second frequency $f_c$. In one example, the second frequency is a frequency to overcome the permittivity of cells in the tumor of the subject's body. As an example, a lower endpoint of a range of the second frequency is between approximately 500 kHz and approximately 1 MHz, and an upper endpoint of a range of the second frequency is between approximately 5 MHz and approximately 50 MHz. In one example, the second frequency is between approximately 500 kHz and approximately 100 MHz. In another example, the second frequency is between approximately 1 MHz and approximately 50 MHz. In another example, the second frequency is between approximately 1 MHz and approximately 10 MHz. In another example, the second frequency is between approximately 1 MHz and approximately 5 MHz. In one example, the second frequency is between approximately 750 kHz to approximately 1250 kHz. In one example, the second frequency is approximately 1 MHz. In one example, the second frequency is between approximately 7.5 MHz to approximately 12.5 MHz. In one example, the second frequency is between approximately 7.5 MHz to approximately 10 MHz. In one example, the second frequency is approximately 10 MHz. The frequency ranges vary according to the electrical properties of the tissues between the transducers and the target, which the carrier frequency seeks to render transparent or minimally obstructive to the transmission of the signal, and the electrical properties of the target, which the TTFields frequency seeks to maximally disrupt. Targets may be the cell membrane or intra-cellular structures such as tubulin, microtubules, actin filaments, organelles, or mitochondrial membranes, for example. In one example, optimal frequencies at which amplitude-modulated TTFields may be applied to kill tumor cells can be refined or modified depending on targets and the most electromagnetic tissue parameter.

In another embodiment, the lower endpoint of a range of the second frequency is between approximately 500 MHz and approximately 1 GHz, and an upper endpoint of a range of the second frequency is between approximately 5 GHz and approximately 10 GHz. In one example, the second frequency is between approximately 500 MHz and approximately 5 GHz. In another example, the second frequency is between approximately 1 GHz and approximately 10 GHz. In comparing the first frequency and the second frequency, the second frequency may be approximately $1 \times 10^1$ times to approximately $1 \times 10^7$ times larger than the first frequency.

Figure 2C:
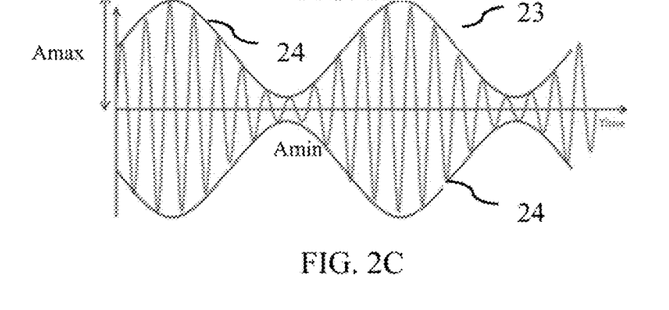

FIG. 2C depicts an example of the amplitude-modulated AC voltage. The amplitude modulated AC voltage 23 is obtained by modulating the amplitude of the second carrier AC voltage 22 by using the amplitude of the first modulating AC voltage 21. The amplitude of the amplitude modulated AC voltage 23 is based on the amplitude of the first modulating AC voltage 21 and the amplitude of the second carrier AC voltage 22. The amplitude of the amplitude modulated AC voltage 23 follows an imaginary envelope 24, which is defined by the amplitude of the first modulating AC voltage 21. The shape of the envelope 24 coordinates with the shape of the first modulating AC voltage 21.

The amplitude of the amplitude modulated AC voltage 23 has a maximum amplitude $A_{max}$ and a minimum amplitude $A_{min}$. The maximum amplitude $A_{max}$ and the minimum amplitude $A_{min}$ may be based on different combinations for the amplitude of the first modulating AC voltage 21 and the amplitude of the second carrier AC voltage 22.

In one example, the maximum amplitude $A_{max}$ and the minimum amplitude $A_{min}$ are obtained using a modulation technique, such as using a modulation index based on the amplitude of the first modulating AC voltage 21 and the amplitude of the second carrier AC voltage 22.

In another example, the maximum amplitude $A_{max}$ and the minimum amplitude $A_{min}$ are obtained by adding and subtracting the amplitude of the first modulating AC voltage 21 and the second carrier AC voltage 22. For example, the maximum amplitude $A_{max}$ and the minimum amplitude $A_{min}$ may satisfy the following equations:

$$A_{max}=A_m+A_c \qquad \text{Equation 1}$$

$$A_{min}=A_m-A_c \qquad \text{Equation 2}$$

As such, the amplitude modulated AC voltage 23 has a first frequency provided by the first modulating AC voltage 21 to produce a frequency for treating the tumor. Furthermore, the amplitude modulated AC voltage 23 has a second frequency provided by the second carrier AC voltage 22 to produce a frequency to overcome the permittivity of the tumor cells and thus improve the intracellular field strength. By applying the modulated electric field to the subject's body as TTFields, it is possible simultaneously to maintain the frequency within the intermediate frequency range for treating tumors and improving the intracellular field intensity in the region of interest of the subject's body, and it is possible to improve the therapeutic effect and efficiency of TTFields.

Referring back to FIG. 1, at step S108, after the first time period, the generation of the first modulated electric field is ceased. To cease generating the first modulated electric field, the voltage generator stops generating the first amplitude modulated AC voltage.

At step S110, a second modulated electric field is generated between the third transducer and the fourth transducer for a second time period. The second modulated electric field is generated by the voltage generator. The second modulated electric field is produced by a second amplitude modulated AC voltage generated by the voltage generator and applied to the second pair of transducers. The amplitude modulated AC voltage may be considered to have a third modulating AC voltage and a fourth carrier AC voltage. The third modulating AC voltage may also be referred to as a third message AC voltage. The amplitude modulated AC voltage is produced by having the third modulating AC voltage modulate the amplitude of the fourth carrier AC voltage. The second modulated electric field is produced using the third transducer, the fourth transducer, and the second amplitude modulated AC voltage.

The second modulated electric field may be produced in a similar manner as described above for the first modulated electric field. In one example, the third modulating AC voltage is capable of producing TTFields with a certain intensity (e.g., 1-20 V/cm) and a first lower frequency range (e.g., 50-500 kHz or 50 kHz-1 MHz), and the fourth carrier AC voltage is capable of producing TTFields with a certain intensity (e.g., 1-20 V/cm) and a second higher frequency range (e.g., 500 kHz-10 GHz or 1 kHz-10 MHz). In one example, the frequency of the third modulating AC voltage is approximately 200 kHz, and the frequency of the fourth carrier AC voltage is approximately 1 MHz. In one example, the electric field strength of the second modulated electric field in the tumor of the subject's body is between approximately 1 V/cm and approximately 20 V/cm. In another example, the electric field strength of the second modulated electric field in the tumor of the subject's body is between approximately 1 V/cm and approximately 4 V/cm. In one example, the transducer may include one or more sensors (e.g., thermistors) to detect the temperature of the tissue in contact with the transducer. The second modulated electric field is generated using the second pair of transducers for the second time period (e.g., one second).

At step S112, after the second time period, the generation of the second modulated electric field is ceased. To cease generating the second modulated electric field, the voltage generator stops generating the second amplitude modulated AC voltage. After the second electric field is ceased, the process repeats in steps S106, S108, S110, S112, and S114.

In other embodiments, more than two pairs of transducers may be used for applying TTFields with modulated electric fields to the subject's body. For example, a plurality of pairs of transducers are located on the subject's body, and modulated electric fields are induced among the plurality of pairs of transducers. In one example, four pairs of transducers with eight transducers may be used. Four modulated electric fields are alternatively induced among four pairs of transducers located on the subject's body. As a specific example of applying TTFields with modulated electric fields to the subject's body among the four pairs of transducers, a first modulated electric field is induced between a first pair of transducers for a first time period. After the first time period, the generation of the first modulated electric field is ceased. A second modulated electric field is induced between a second pair of transducers for a second time period. After the second time period, the generation of the second modulated electric field is ceased. A third modulated electric field is induced between a third pair of transducers for a third time period. After the third time period, the generation of the third modulated electric field is ceased. A fourth modulated electric field is induced between a fourth pair of transducers for a fourth time period. After the fourth time period, the generation of the fourth modulated electric field is ceased. After the fourth electric field is ceased, the process repeats the steps from inducing the first modulated electric field between the first pair of transducers to inducing the fourth modulated electric field between the fourth pair of transducers.

Figure 3A:
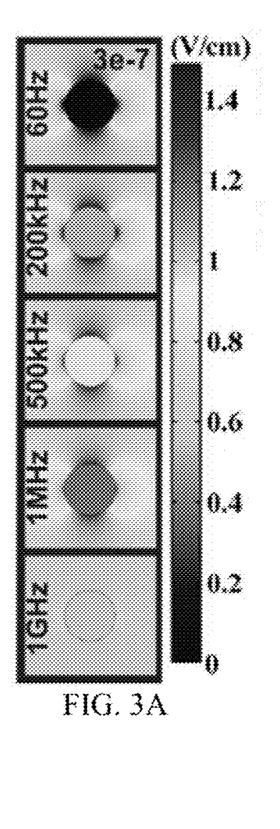
FIGS. 3A-3C depict simulation results of intracellular field strength when electric fields with different frequencies are applied to a cell.
Figure 3B:
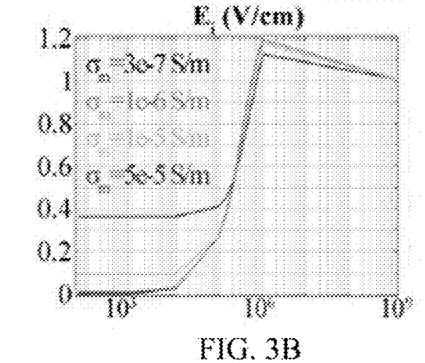
Figure 3C:
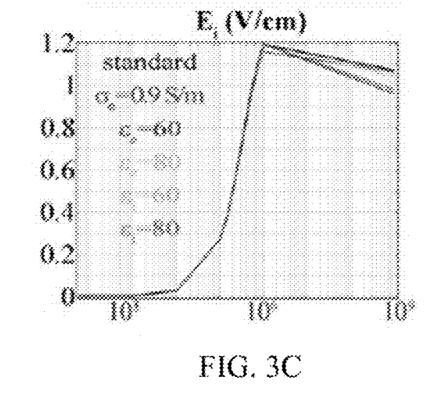

FIGS. 3A, 3B, and 3C depict simulation results of intracellular field strength when electric fields with different frequencies are applied to a cell. With a finite element method simulation, the impact of the TTFields on a spherical cell during metaphase can be determined. FIG. 3A is a surface plot of the electric field for different frequencies of the TTFields. The circle in the center of each square represents a simulated cell with a 10 μm radius, and the colors inside and outside the circle represent the strength of the electric field (V/cm) according to the color scale on the right. Each square is the result from simulating TTFields with a field strength of 1 V/cm at different frequencies (e.g., at 60 Hz, 200 kHz, 500 kHz, 1 MHz, and 1 GHz). As the frequency of the TTFields changes, the electric field distribution and the intracellular field strength are changed.

With reference to FIG. 3A, when the frequency of the electric field is 60 Hz, the field strength inside the cell walls almost equals zero, and the cell is virtually unaffected by the electric field. When the frequency of the electric field is increased to 200 kHz, an increase of intracellular field strength is observed, and the field strength is approximately 0.5 V/cm. The field strength increases as the frequency of the electric field increases above this value. When the frequency of the electric field is increased to 500 kHz, an increase of intracellular field strength is observed, and the field strength is approximately 0.95 V/cm. When the frequency of the electric field is 1 MHz, the field strength inside the cell walls is higher than the field strength outside the cell walls, and the intracellular field strength is approximately 1.2 V/cm. As such, at 1 MHz, the simulated cell is absorbing and retaining more of the electric field inside the cell than is outside the cell. When the frequency of the electric field is increased to 1 GHz, the field strength inside and outside the cell walls is the same, and the cellular structure becomes "electrically invisible."

FIG. 3B is a plot of the intracellular electric field strength as a function of frequency versus conductivity. The conductivity of the cell membrane $\sigma_m$ was varied, and the effects of these different conductivities are reflected in different plots for the intracellular electric field strength. The simulated conductivities of the cell membrane $\sigma_m$ in Siemens/meter (S/m) are 5e-5 S/m, 1e-5 S/m, 1e-6 S/m, and 3e-7 S/m. At approximately 500 kHz, the intracellular electric field strengths are approximately 0.95 V/cm to 1.25 V/cm. At approximately 1 MHz, the intracellular electric field strength peaks at approximately 1.1 V/cm to 1.2 V/cm. At frequencies above 1 MHz to approximately 100 MHz, the intracellular electric field strength is above approximately 1.05 V/cm.

FIG. 3C is another plot of the intracellular electric field strength as a function of frequency versus relative permittivity. The conductivity of the extracellular space $\sigma_e$, the permittivity of the extracellular space $\varepsilon_e$, and the permittivity of the cytoplasm $\varepsilon_i$ were varied, and the effects of these changes are reflected in different plots for the intracellular electric field strength. The simulated conductivity of the extracellular space $\sigma_e$ was fixed at 0.9 S/m, the simulated permittivity of the extracellular space $\varepsilon_e$ was 60 and 80, and the simulated permittivity of the cytoplasm $\varepsilon_i$ was 60 and 80. At approximately 500 kHz, the intracellular electric field strengths are approximately 1.0 V/cm. At approximately 1 MHz, the intracellular electric field strength peaks at approximately 1.15 V/cm to 1.2 V/cm. At frequencies above 1 MHz to approximately 100 MHz, the intracellular electric field strength is above approximately 1.05 V/cm and below a critical value predicted at 1.2 V/cm, and the intracellular electric field strength in the simulation decreases for the conductivity and permittivity combinations in a frequency-dependent manner.

Figure 3D:
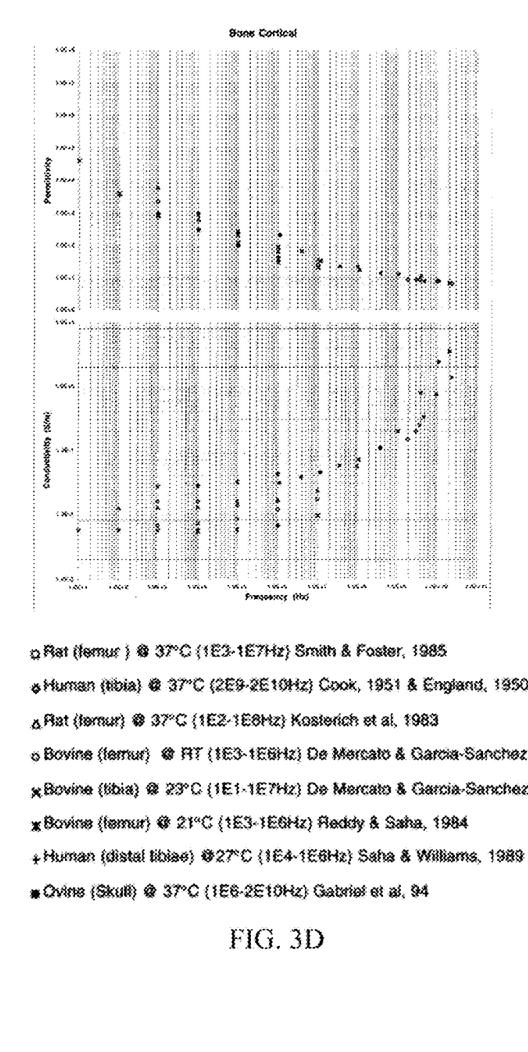
FIG. 3D depicts the dielectric properties of bone cortical tissue as a function of frequency.

FIG. 3D is a plot of the dielectric properties of bone cortical tissue as a function of frequency. The dielectric properties of materials may be obtained from measured complex relative permittivity and based on the following equation:

$$\varepsilon_r = \varepsilon' - j\varepsilon'' \quad \text{Equation 3}$$

where $\varepsilon_r$ is the permittivity of a material, $\varepsilon'$ is the relative permittivity of the material, $\varepsilon''$ is the out-of-phase loss factor, and j is a constant.

Furthermore, the out-of-phase loss factor $\varepsilon''$ may satisfy the following equation:

$$\varepsilon'' = \sigma/\varepsilon_0 \omega \quad \text{Equation 4}$$

where $\sigma$ is the total conductivity of the material, Co is the permittivity of free space, and $\omega$ is the angular frequency of the electric field. In one example, the conductivity of the material $\sigma$ may be in units of siemens per meter (S/m).

The permittivity and conductivity of bone cortical tissue as a function of the frequency of the electric fields are presented in FIG. 3D. The data of the permittivity and conductivity as a function of the frequency in human, rat, bovine, and ovine were extracted from several studies. The permittivity of the bone cortical in human, rat, bovine, and ovine decreases as the frequency of the electric field increases. The conductivity of the bone cortical increases as the frequency of the electric field increases. When the frequency of the electric field is within 1.0E+1 to 1.0E+6 Hz (i.e., 1 Hz to 1 MHz), the conductivity of the bone cortical tissue increases as the frequency of the electric field increases, but the increase is slow. When the frequency of the electric field is increased above 1.0E+6 Hz (i.e., 1 MHz), the slope of the plot is larger compared to the slope of the frequency of the electric field below 1 MHz, indicating the conductivity of the bone cortical tissue increases more rapidly as the frequency of the electric field increase above 1 MHz. The results suggest the therapeutic effect of TTFields is field strength-dependent and frequency-dependent. The alternating electric fields with frequency within the intermediate frequency range (e.g., 50-500 kHz) can significantly reduce cell proliferation. In order for TTFields to exert a therapeutic effect, field intensities should exceed a threshold of approximately 1 V/cm and that efficacy in killing cancer cells increases significantly—at least linearly and perhaps quadratically—with increasing field strength above 1 V/cm and 2-4 changes of direction of the applied field per second.

As shown in FIGS. 3A, 3B, and 3C, the intracellular field strength produced from TTFields with an intensity of 1 V/cm and with a desirable intermediate frequency (e.g., 50-500 kHz or 50 kHz-1 MHz) may not be able to reach a field intensity of 1 V/cm or higher. Having an intracellular field strength of 1 V/cm or higher would be desirable to treat tumors with TTFields. As shown in FIG. 3D, the conductivity of biological tissue is low when the frequency of the electric field is below 1 MHz. The inventor solved the problem of how to provide a higher dose of TTFields at the desirable frequency range to a tumor in a subject's body. In particular, the inventor discovered that applying TTFields with amplitude-modulated electric fields provides a higher dose of TTFields at the desirable frequency range to the tumor in the subject's body. With the invention, the frequency of the TTFields is maintained within the desired frequency range, and the intracellular field strength reaches a desired level in the region of interest of the subject's body.

Figure 4:
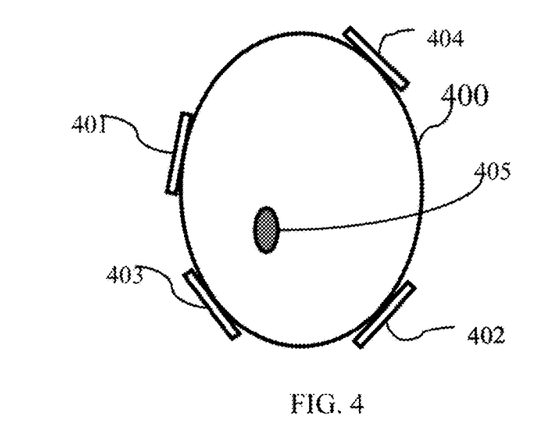
FIG. 4 depicts an example of a transducer layout for applying TTFields with modulated electric fields to the head of a subject's body.

FIG. 4 depicts an example of a transducer layout for applying TTFields with modulated electric fields to the head of a subject's body. In some embodiments, two pairs of transducers with a total of four transducers are used for applying TTFields to the subject's body.

In FIG. 4, the transducer layout has four transducers for applying TTFields with modulated electric fields to the head of the subject's body. The first transducer 401, the second transducer 402, the third transducer 403, and the fourth transducer 404 are located on the subject's head 400 for applying modulated electric fields to the region of interest 405 (e.g., a tumor in the subject's body). In one example, the region of interest is identified by non-invasive imaging technology, e.g., magnetic resonance imaging (MRI). In one example, the first transducer 401 and the third transducer 403 are located on the left side of the region of interest 405, and the second transducer 402 and the fourth transducer 404 are located on the right side of the region of interest 405. As to pairs, the first transducer 401 and the second transducer 402 may form a first pair of transducers, and the third transducer 403 and the fourth transducer 404 may form a second pair of transducers. The structures of the transducers are not limited to the described embodiments, and a further discussion of exemplary transducers is provided below and depicted in FIGS. 6A-6D.

Figure 5:
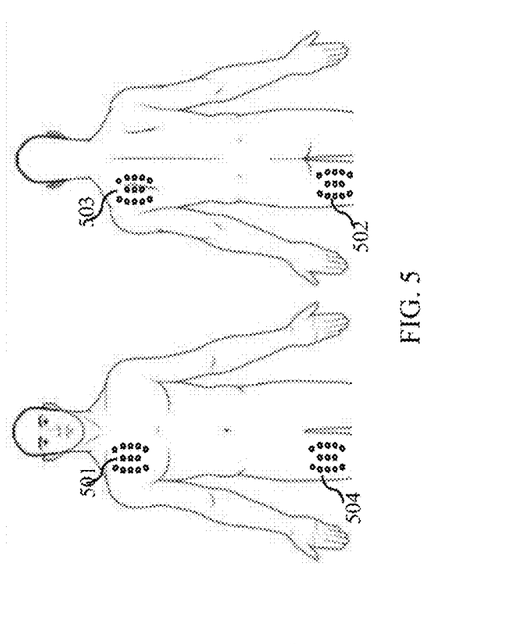
FIG. 5 depicts an example of transducer layouts with two pairs of transducers for applying TTFields with modulated electric fields to the torso of the subject's body.

FIG. 5 depicts an example of a transducer layout with two pairs of transducers for applying TTFields with modulated electric fields to the torso of a subject's body. In some embodiments, two pairs of transducers with a total of four transducers are used for applying TTFields to the subject's body.

In the example depicted in FIG. 5, the first transducer 501 is located on the front of the right thorax, and the second transducer 502 is located on the back of the left thigh. Furthermore, the third transducer 503 is located on the back of the left thorax, and the fourth transducer 504 is located on the front of the right thigh. As to pairs, the first transducer 501 and the second transducer 502 may form a first pair of transducers, and the third transducer 503 and the fourth transducer 504 may form a second pair of transducers. In another example, the first transducer 501 and the fourth transducer 504 may form a first pair of transducers, and the third transducer 503 and the second transducer 502 may form a second pair of transducers. In one example, a first modulated electric field is generated between a first pair of transducers, and a second modulated electric field is generated between a second pair of transducers.

In another example, the first and second modulated electric fields may be generated using parts of the transducers. For example, a first modulated electric field may be generated between a first part of the first transducer and a first part of the second transducer, and a second modulated electric field may be generated between a second part of the first transducer and a second part of the second transducer. In one example, the first part of the first transducer does not overlap with the second part of the first transducer. In one example, the first part of the first transducer may partially overlap with the second part of the first transducer. In one example, the first part of the second transducer does not overlap with the second part of the second transducer. In one example, the first part of the second transducer may partially overlap with the second part of the second transducer.

In some embodiments, the modulated electric field may be generated using a single transducer. In a more specific example, the modulated electric field comprising two frequencies is transmitted through tissue to a target region of the subject's body, and the tissue's ability to absorb current can be used as the electrical ground for the circuit.

In other embodiments, the two modulated electric fields may be generated using two or more transducers, and more than two pairs of transducers may be used for applying TTFields with modulated electric fields to a subject's body. For example, a plurality of pairs of transducers are located on the subject's body, and modulated electric fields are induced among various combinations of the plurality of pairs. For example, four pairs of transducers with eight transducers may be used. In this example, the first modulated electric field is induced between the first pair of transducers, the second modulated electric field is induced between the second pair of transducers, the third modulated electric field is induced between the third pair of transducers, and the fourth modulated electric field is induced between the fourth pair of transducers.

FIGS. 6A-6D are examples of the structure of a transducer. For example, the transducer 60A has a substrate 61A and a plurality of electrode elements 62A. The substrate 61A is configured for attaching the transducers to a subject's body. Suitable materials for the substrate 61A include, for example, cloth, foam, and flexible plastic. In one example, the substrate 61A includes a conductive medical gel having a thickness of not less than approximately 0.5 mm. In a more specific example, the substrate 61A is a layer of hydrogel with a minimum thickness of 0.5 mm. The transducer 60A is attached to the subject's body through the substrate 61.

Figure 6A:
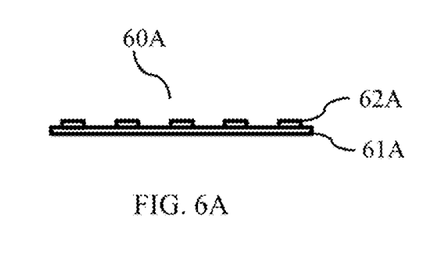
FIGS. 6A-6D depict examples of the structure of a transducer.

A plurality of capacitively coupled electrode elements 62A are positioned on the substrate 61A, and each of the capacitively coupled electrode elements has a conductive plate with a dielectric layer disposed thereon that faces towards the substrate. Optionally, one or more sensors (e.g., temperature sensor) may be positioned beneath each of the electrode elements in a manner that is similar to the conventional arrangement used in the Novocure Optune® system.

Figure 6B:
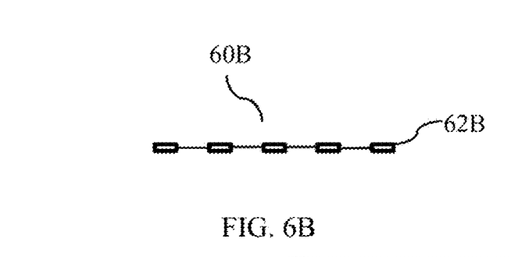

FIG. 6B depicts another example of the structure of the transducer 60B. In one example, the transducer 60B is a grouping of electrodes. In this example, the transducer 60B includes a plurality of electrode elements 62B. The plurality of electrode elements 62B is electrically and mechanically connected to one another without a substrate. In one example, the electrode elements 62B are connected to one another through conductive wires.

Figure 6C:
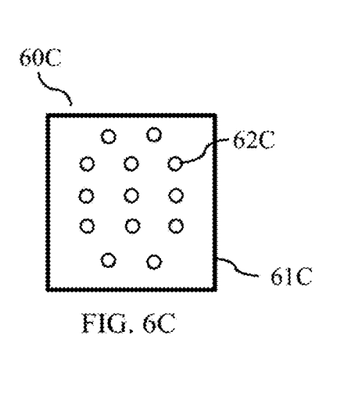
Figure 6D:
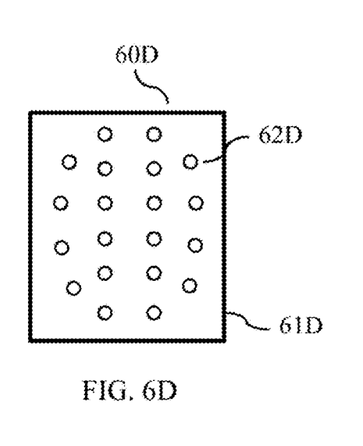

FIGS. 6C and 6D are further examples of the structure of the transducer. The transducer may include any desired number of electrode elements 62C on the substrate 61C or an array 62D on the substrate 61D.

In one example, the electrode elements 62A, 62B, 62C, 62D are ceramic disks, and each of the ceramic disks is approximately 2 cm in diameter and approximately 1 mm in thickness. In another example, the electrode elements 62A, 62B, 62C, 62D are ceramic elements that are not disk-shaped. In another example, the electrode elements 62A, 62B, 62C, 62D are non-ceramic dielectric materials (e.g., polymer films) positioned over a plurality of flat conductors. Various shapes, sizes, and materials can be used for the electrode elements.

In alternative embodiments, the transducer may include only one single electrode element. In one example, the single electrode element is a flexible organic material or flexible organic composite positioned on a substrate. In another example, the transducer may include a flexible organic material or flexible organic composite without a substrate.

In other alternative embodiments, composite transducers with each composite transducer comprising two or more transducers may be used to apply the modulated electric fields. In one example, each composite transducer includes a first transducer and a second transducer, and the first and second transducer of the composite transducer have different materials and/or structures. In a more specific example, the first transducer of the composite transducer is composed of materials and a structure optimally that transmits the first frequency to the target region, and the second transducer of the composite transducer is composed of materials and a structure that optimally transmits the second frequency to the target region.

Other alternative constructions for implementing the transducer for use with embodiments of the invention may also be used, as long as they are capable of (a) delivering TTFields with modulated electric fields to the subject's body and (b) being positioned at the locations specified herein.

Figure 7:
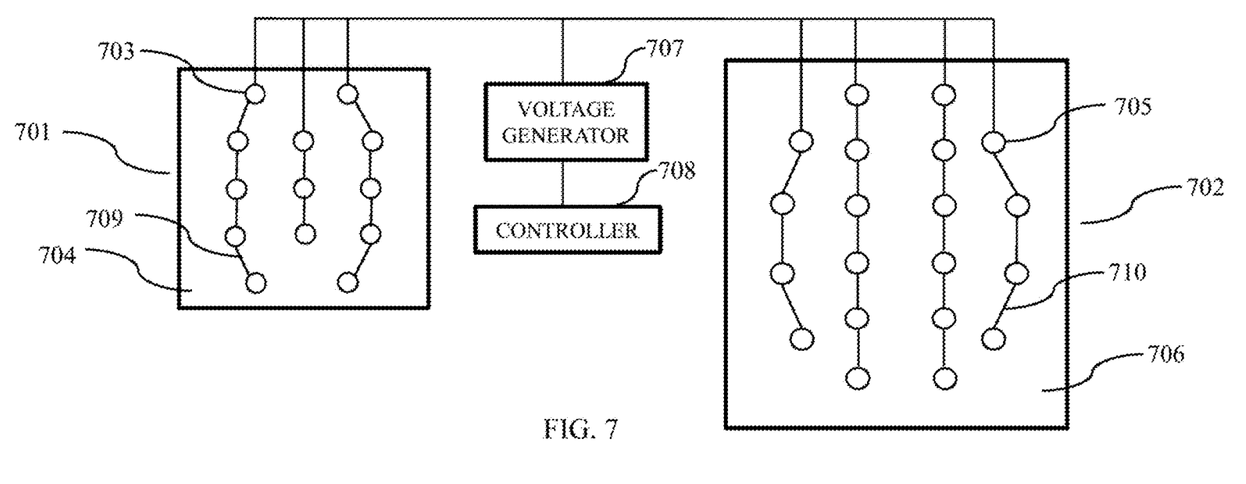
FIG. 7 depicts one example of an apparatus to apply TTFields with modulated electric fields to a subject's body.

FIG. 7 depicts one example of an apparatus to apply TTFields with modulated electric fields to a subject's body. The first transducer 701 includes 13 electrode elements 703, which are positioned on the substrate 704, and the electrode elements 703 are electrically and mechanically connected to one another through a conductive wiring 709. The second transducer 702 includes 20 electrode elements 705, which are positioned on the substrate 706, and the electrode elements 705 are electrically and mechanically connected to one another through a conductive wiring 710. The first transducer 701 and the second transducer 702 are connected to an AC voltage generator 707 and a controller 708. The controller 708 may include one or more processors and memory accessible by the one or more processors. The memory may store instructions that when executed by the one or more processors, control the AC voltage generator 707 to implement one or more embodiments of the invention. In some embodiments, the AC voltage generator 707 and the controller 708 may be integrated in the first transducer 701 and the second transducer 702 and form a first electric field generator and a second electric field generator.

Figure 8:
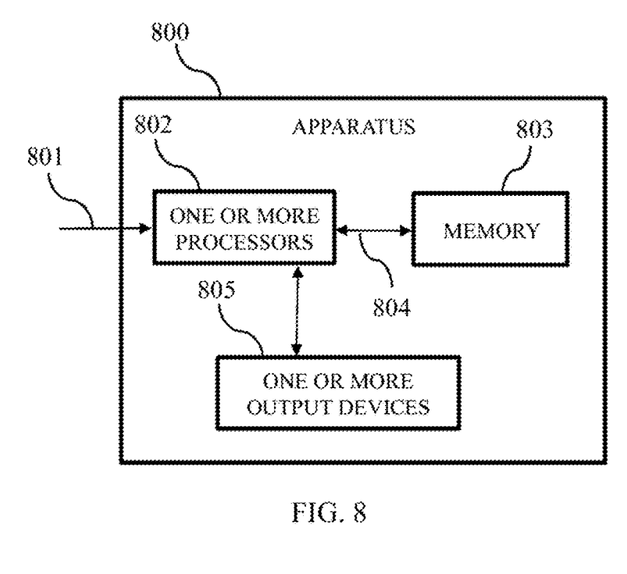
FIG. 8 depicts one example of a controller apparatus to apply TTFields with modulated electric fields to a subject's body.

FIG. 8 depicts one example of a controller apparatus to apply TTFields with modulated electric fields for the embodiments herein. The controller apparatus 800 may be used as the controller 708 and includes one or more processors 802, one or more output devices 805, and a memory 803.

In one example, based on input 801, the one or more processors generate control signals to control the voltage generator to implement an embodiment of the invention. In one example, the input 801 is user input. In another example, the input 801 may be from another computer in communication with the controller apparatus 800. The output devices 805 may provide the status of the operation of the invention, such as transducer selection, voltages being generated, and other operational information.

The memory 803 is accessible by the one or more processors 802 via the link 804 so that the one or more processors 802 can read information from and write information to the memory 803. The memory 803 may store instructions that when executed by the one or more processors 802 implement one or more embodiments of the invention.

In some embodiments, the frequency of the carrier signal can vary. For example, the frequency of the carrier signal can be from approximately 1 MHz to approximately 10 MHz. The frequencies of the carrier signal and TTFields can be obtained from the following equation:

$$\frac{V_a}{2}(\cos 2\pi f_1 t + \cos 2\pi f_2 t) = \quad \text{Equation 5}$$

$$V_a \cdot \cos\left(2\pi \frac{f_1 + f_2}{2} t\right) \cdot \cos\left(2\pi \frac{f_1 - f_2}{2} t\right)$$

where $V_a$ is a voltage amplitude that induces an electric field of $$1 \frac{V}{cm}$$

amplitude. The two solutions in the frequency domain can be summed to get the desired solution instead of simulating at the time domain.

Figure 9A:
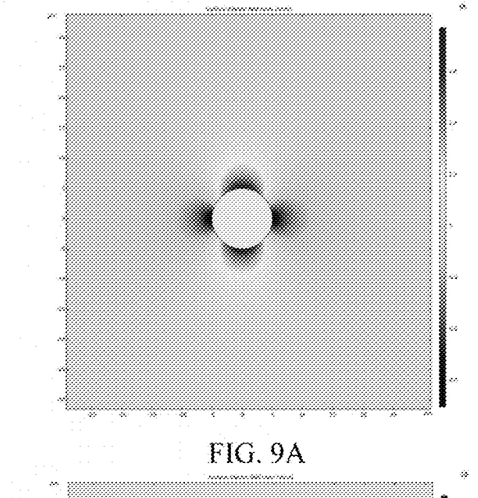
FIGS. 9A and 9B depict simulation results of intracellular field strength when electric fields with different frequencies of the carrier signal and TTFields are applied to a cell.
Figure 9B:
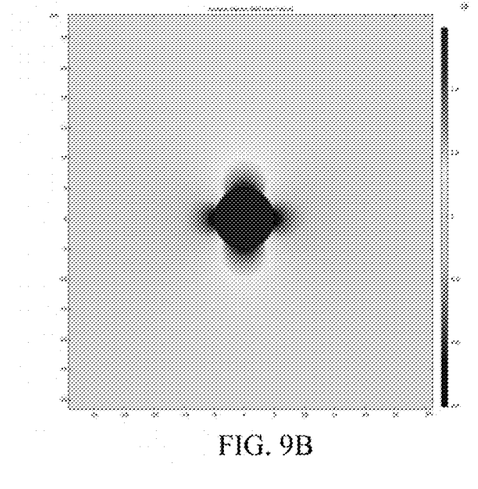

FIGS. 9A-9B are surface plots of the electric field for different frequencies of the carrier signals. With reference to FIG. 9A, the frequencies of the carrier signal (e.g., 1 MHz here) and the message (i.e., TTFields) signal (e.g., 200 kHz here) that satisfy the following equation was used:

$$\begin{cases} \frac{f_1 + f_2}{2} = 1\,\text{MHz} \\ \frac{f_1 - f_2}{2} = 200\,\text{kHz} \end{cases} \rightarrow \begin{cases} f_1 = 1.2\,\text{MHz} \\ f_2 = 800\,\text{kHz} \end{cases} \quad \text{Equation 5}$$

When the frequency of the carrier signal is 1 MHz, the frequency of TTFields is 200 kHz, and the field strength is approximately 1.2 V/cm. Compared to the field strength without carrier signals (i.e., approximately 0.18 V/cm), an increase of intracellular field strength is observed. As an external field of 1V/cm was applied, the penetration rate is also improved (i.e., approximately 120% field penetration). With reference to FIG. 9B, the frequencies of the carrier signal (e.g., 10 MHz here) and the message (i.e., TTFields) (e.g., 200 kHz here) that satisfy the following equation were used:

$$\begin{cases} \frac{f_1 + f_2}{2} = 10\,\text{MHz} \\ \frac{f_1 - f_2}{2} = 200\,\text{kHz} \end{cases} \rightarrow \begin{cases} f_1 = 10.2\,\text{MHz} \\ f_2 = 9.8\,\text{kHz} \end{cases} \quad \text{Equation 6}$$

When the frequency of the carrier signal is 10 MHz, the frequency of TTFields is 200 kHz, and the field strength is approximately 1.5 V/cm. Compared to the field strength without carrier signals (i.e., approximately 0.18 V/cm) and with 1 MHz of the carrier signal, an increase of intracellular field strength (i.e., approximately 1.5 V/cm) and penetration rate (i.e., approximately 150% field penetration) are observed.

The invention includes other illustrative embodiments, such as the following.

Illustrative Embodiment 1. A method of applying tumor treating fields to a subject's body, the method comprising: locating a first transducer at a first location of the subject's body; locating a second transducer at a second location of the subject's body; and inducing a modulated electric field between at least part of the first transducer and at least part of the second transducer.

Illustrative Embodiment 2. The method of Illustrative Embodiment 1, wherein the first transducer and the second transducers are capacitively coupled.

Illustrative Embodiment 3. The method of Illustrative Embodiment 1, wherein the first transducer comprises a first array of substantially electrode elements, and the second transducer comprises a second array of substantially electrode elements.

Illustrative Embodiment 4. The method of Illustrative Embodiment 3, wherein the first array of substantially electrode elements comprises a first plurality of ceramic disks, each of the first plurality of ceramic disks is approximately 2 cm in diameter and approximately 1 mm in thickness, a number of the first plurality of ceramic disks is between 13 and 20; and wherein the second array of substantially electrode elements comprises a second plurality of ceramic disks, each of the second plurality of ceramic disks is approximately 2 cm in diameter and approximately 1 mm in thickness, a number of the second plurality of ceramic disks is between 13 and 20.

Illustrative Embodiment 5. The method of Illustrative Embodiment 1, wherein the first transducer covers a surface area of approximately 140 to 250 cm$^2$, and the second transducer covers a surface area of approximately 140 to 250 cm$^2$.

As an example, if the first transducer has array of 13 electrode elements and is oval shaped with a length of 5 transducers spaced 2 cm apart and with a width of 3 transducers spaced 2 cm apart, and if each transducer is 2 cm in diameter, a length of the first transducer is 18 cm, and a width of the first transducer is 10 cm. As such, an area of the first transducer is 9 cm×5 cm×pi=141.4 cm$^2$.

As an example, if the first transducer has an array of 20 electrode elements and is oval shaped with a length of 6 transducers spaced 2 cm apart and with a width of 4 transducers spaced 2 cm apart, and if each transducer is 2 cm in diameter, a length of the first transducer is 22 cm, and a width of the first transducer is 14 cm. As such, an area of the first transducer is 11 cm×7 cm×pi=241.9 cm$^2$.

Illustrative Embodiment 6. The method of Illustrative Embodiment 1, wherein the first transducer and the second transducer are non-conductive.

Illustrative Embodiment 7. A method of applying tumor treating fields to a subject's body, the method comprising: alternately generating a first modulated electric field with a first pair of transducers for a first time period and a second modulated electric field with a second pair of transducers for a second time period, wherein the first pair of transducers is located at a first location and a second location of the subject's body, and wherein the second pair of transducers is located at a third location and a fourth location of the subject's body.

Illustrative Embodiment 8. A method of applying tumor treating fields to a subject's body, the method comprising: inducing a modulated electric field between a first electric field generator and a second electric field generator, wherein the first electric field generator is situated at a first location of the subject's body, wherein the second electric field generator is situated at a second location of the subject's body, and wherein the modulated electric field comprises a first signal having a first frequency and a second signal having a second frequency, the first frequency being between approximately 100 kHz and approximately 500 kHz, the second frequency being between approximately 1 MHz and approximately 10 GHz, and the first signal modulating the second signal.

Illustrative Embodiment 9. A method of applying tumor treating fields to a torso of a subject's body, the method comprising: generating an electric field between a first grouping of electrodes and a second grouping of electrodes, the electric field having two simultaneous frequencies, wherein the first grouping of electrodes is affixed at a first location on the subject's body, and wherein the second grouping of electrodes is affixed at a second location on the subject's body.

Illustrative Embodiment 10. A method of applying tumor treating fields to a subject's body, the method comprising: inducing a modulated electric field between a first transducer and a second transducer to treat a tumor of the subject's body, wherein the first transducer is located at a first location of the subject's body, and wherein the second transducer is located at a second location of the subject's body.

Illustrative Embodiment 11. The method of Illustrative Embodiment 10, wherein the modulated electric field is induced by applying an amplitude modulated AC voltage to the first and second transducers, and wherein the amplitude modulated AC voltage comprises a first frequency and a second frequency, and the first frequency is smaller than the second frequency.

Illustrative Embodiment 12. The method of Illustrative Embodiment 11, wherein the first frequency of the amplitude modulated AC voltage is between approximately 100 kHz and approximately 500 kHz, and the second frequency of the amplitude modulated AC voltage is between approximately 500 kHz and approximately 10 GHz.

Illustrative Embodiment 13. The method of Illustrative Embodiment 11, wherein the first frequency of the first electric field is between approximately 100 kHz and approximately 500 kHz, and wherein the second frequency of the second electric field is between approximately 1 MHz and approximately 5 MHz.

Illustrative Embodiment 14. The method of Illustrative Embodiment 10, wherein the modulated electric field in the tumor of the subject's body is between approximately 1 V/cm and approximately 20 V/cm.

Illustrative Embodiment 15. The method of Illustrative Embodiment 10, wherein the modulated electric field in the tumor of the subject's body is between approximately 1 V/cm and approximately 4 V/cm.

Illustrative Embodiment 16. The method of Illustrative Embodiment 10, wherein the modulated electric field comprises a first frequency and a second frequency, the first frequency being a frequency to disrupt mitosis in the tumor of the subject's body, and the second frequency being a frequency to attenuate obstructive effects of frequency-dependent electric tissue properties.

Illustrative Embodiment 17. The method of Illustrative Embodiment 16, wherein the obstructive effects of frequency-dependent electric tissue properties include permittivity and/or conductivity effects of tissues between the first transducer, the second transducer and the tumor of the subject's body, and wherein the obstructive effects of frequency-dependent electric tissue properties reduce electric field strength at a target site in a region of the tumor.

Illustrative Embodiment 18. The method of Illustrative Embodiment 10, wherein the modulated electric field comprises: a first frequency to treat the tumor of the subject's body; and a second frequency selected to produce a modulated electric field strength larger inside cell walls of the tumor of the subject's body than outside the cell walls of the tumor of the subject's body.

Illustrative Embodiment 19. The method of Illustrative Embodiment 10, wherein the modulated electric field comprises a first signal having a first frequency to disrupt mitosis in the tumor of the subject's body and a second signal being a carrier signal modulated by the first signal, the second signal having a frequency to penetrate cell walls of the tumor of the subject's body.

Illustrative Embodiment 20. The method of Illustrative Embodiment 10, wherein the modulated electric field is induced in a head of the subject's body of the subject's body or in a torso of the subject's body of the subject's body.

Illustrative Embodiment 21. The method of Illustrative Embodiment 10, the method further comprises alternately inducing the modulated electric field between the first transducer and the second transducer and inducing a second modulated electric field between a third transducer and a fourth transducer, wherein the third transducer is located at a third location of the subject's body, and wherein the fourth transducer is located at a fourth location of the subject's body.

Illustrative Embodiment 22. The method of Illustrative Embodiment 10, wherein the modulated electric field and the second modulated electric field each comprise a first frequency for treating a tumor in the subject's body and a second frequency, wherein the first frequency is less than the second frequency.

Illustrative Embodiment 23. A method of applying tumor treating fields to a subject's body, the method comprising: inducing a modulated electric field between a first electric field generator and a second electric field generator, wherein the first electric field generator is situated at a first location of the subject's body, wherein the second electric field generator is situated at a second location of the subject's body, and wherein the modulated electric field comprises a first signal having a first frequency and a second signal having a second frequency, the first frequency being between approximately 100 kHz and approximately 500 kHz, the second frequency being between approximately 500 kHz and approximately 10 GHz, and the first signal modulating the second signal.

Illustrative Embodiment 24. The method of Illustrative Embodiment 23, wherein the second frequency is between approximately 1 MHz and approximately 10 GHz.

Illustrative Embodiment 25. An apparatus to apply tumor treating fields to a torso of a subject's body, the apparatus comprising: a first transducer adapted to be located at a first location of the subject's body; a second transducer adapted to be located at a second location of the subject's body; a voltage generator adapted to be coupled to the first transducer and the second transducer to be capable of providing voltage to the first transducer and the second transducer; and a controller coupled to the voltage generator, the controller comprising one or more processors and memory accessible by the one or more processors, the memory storing instructions that when executed by the one or more processors, cause the controller to: instruct the voltage generator to generate a voltage signal for the first transducer and the second transducer to induce a modulated electric field in the subject's body, the voltage signal comprising a message signal at a first frequency and a carrier signal at a second frequency, the first frequency being a frequency to treat a tumor in the subject's body, the message signal modulating the carrier signal.

Illustrative Embodiment 26. The apparatus of Illustrative Embodiment 25, wherein the first frequency is between approximately 100 kHz and approximately 500 kHz, and the second frequency is between approximately 500 kHz and approximately 10 GHz.

Illustrative Embodiment 27. The apparatus of Illustrative Embodiment 25, wherein the first transducer and the second transducer are capacitively coupled.

Illustrative Embodiment 28. The apparatus of Illustrative Embodiment 27, wherein the first transducer comprises a first array of substantially flat electrode elements, and the second transducer comprises a second array of substantially flat electrode elements.

Illustrative Embodiment 29. The apparatus of Illustrative Embodiment 25, wherein the first transducer and the second transducer are non-conductive.

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A method of applying tumor treating fields to a subject's body, the method comprising:
   inducing a modulated electric field between a first transducer and a second transducer to treat a tumor of the subject's body,
   wherein the first transducer is located at a first location of the subject's body, and
   wherein the second transducer is located at a second location of the subject's body,
   wherein the modulated electric field comprises a first frequency and a second frequency, the first frequency being a frequency to disrupt mitosis in the tumor of the subject's body, and the second frequency being a frequency to attenuate obstructive effects of frequency-dependent electric tissue properties,
   wherein the modulated electric field is induced by applying an amplitude modulated AC voltage to the first and second transducers, and
   wherein the amplitude modulated AC voltage comprises the first frequency and the second frequency, and the first frequency is smaller than the second frequency,
   wherein the second frequency of the amplitude modulated AC voltage is between 500 kHz and 10 GHz.

2. The method of claim 1, wherein the first frequency of the amplitude modulated AC voltage is between 100 kHz and 500 kHz.

3. The method of claim 1, wherein the first frequency of the first electric field is between 100 kHz and 500 kHz, and wherein the second frequency of the second electric field is between 1 MHz and 5 MHz.

4. The method of claim 1, wherein the modulated electric field in the tumor of the subject's body is between 1 V/cm and 20 V/cm.

5. The method of claim 1, wherein the modulated electric field in the tumor of the subject's body is between 1 V/cm and 4 V/cm.

6. The method of claim 1, wherein the obstructive effects of frequency-dependent electric tissue properties include permittivity and/or conductivity effects of tissues between the first transducer, the second transducer and the tumor of the subject's body, and
   wherein the obstructive effects of frequency-dependent electric tissue properties reduce electric field strength at a target site in a region of the tumor.

7. The method of claim 1, wherein
   the first frequency further being a frequency to treat the tumor of the subject's body; and
   the second frequency further being selected to produce a modulated electric field strength larger inside cell walls of the tumor of the subject's body than outside the cell walls of the tumor of the subject's body.

8. The method of claim 1, wherein the modulated electric field comprises a first signal having a first frequency to disrupt mitosis in the tumor of the subject's body and a second signal being a carrier signal modulated by the first signal, the second signal having a frequency to penetrate cell walls of the tumor of the subject's body.

9. The method of claim 1, wherein the modulated electric field is induced in a head of the subject's body of the subject's body or in a torso of the subject's body of the subject's body.

10. The method of claim 1, further comprising:
    alternately inducing the modulated electric field between the first transducer and the second transducer and inducing a second modulated electric field between a third transducer and a fourth transducer,
    wherein the third transducer is located at a third location of the subject's body, and
    wherein the fourth transducer is located at a fourth location of the subject's body.

11. The method of claim 10, wherein the modulated electric field and the second modulated electric field each comprise the first frequency for treating a tumor in the subject's body and the second frequency, wherein the first frequency is less than the second frequency.

12. A method of applying tumor treating fields to a subject's body, the method comprising:
    inducing a modulated electric field between a first electric field generator and a second electric field generator,
    wherein the first electric field generator is situated at a first location of the subject's body, wherein the second electric field generator is situated at a second location of the subject's body, and wherein the modulated electric field comprises a first signal having a first frequency and a second signal having a second frequency, the first frequency being between 100 kHz and 500 kHz, the second frequency being between 500 kHz and 10 GHZ, and the first signal modulating the second signal, wherein the first frequency being a frequency to disrupt mitosis in the tumor of the subject's body, and the second frequency being a frequency to attenuate obstructive effects of frequency-dependent electric tissue properties.

13. The method of claim 12, wherein the second frequency is between 1 MHz and 10 GHz.

14. An apparatus to apply tumor treating fields to a torso of a subject's body, the apparatus comprising:

a first transducer adapted to be located at a first location of the subject's body;

a second transducer adapted to be located at a second location of the subject's body;

a voltage generator adapted to be coupled to the first transducer and the second transducer to be capable of providing voltage to the first transducer and the second transducer; and a controller coupled to the voltage generator, the controller comprising one or more processors and memory accessible by the one or more processors, the memory storing instructions that when executed by the one or more processors, cause the controller to:

instruct the voltage generator to generate a voltage signal for the first transducer and the second transducer to induce a modulated electric field in the subject's body, the voltage signal comprising a message signal at a first frequency and a carrier signal at a second frequency, the first frequency being a frequency to treat a tumor in the subject's body, the message signal modulating the carrier signal, and the second frequency being a frequency to attenuate obstructive effects of frequency-dependent electric tissue properties, wherein the second frequency is between 500 kHz and 10 GHz.

15. The apparatus of claim 14, wherein the first frequency is between 100 kHz and 500 kHz.

16. The apparatus of claim 14, wherein the first transducer and the second transducer are capacitively coupled.

17. The apparatus of claim 14, wherein the first transducer comprises a first array of flat electrode elements, and the second transducer comprises a second array of flat electrode elements.

18. The apparatus of claim 14, wherein the first transducer and the second transducer are non-conductive.

19. The method of claim 1, wherein the second frequency of the amplitude modulated AC voltage is between 1 MHz and 10 GHz.

20. The method of claim 1, wherein the first location of the first transducer is on the subject's body, and wherein the second location of the second transducer is on the subject's body.

* * * * *